(12) United States Patent
Moesinger

(10) Patent No.: US 6,326,016 B2
(45) Date of Patent: *Dec. 4, 2001

(54) PLANT IMMUNIZATION COMPOSITIONS

(75) Inventor: Egon Moesinger, Reute (DE)

(73) Assignee: Syngenta Investment Corporation, Wilmington, DE (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/194,497

(22) PCT Filed: May 27, 1997

(86) PCT No.: PCT/EP97/02744

§ 371 Date: Nov. 25, 1998

§ 102(e) Date: Nov. 25, 1998

(87) PCT Pub. No.: WO97/45018

PCT Pub. Date: Dec. 4, 1997

(30) Foreign Application Priority Data

May 28, 1996 (GB) .................................... 9611089

(51) Int. Cl.⁷ .......................... A01N 25/00; A01N 63/04; C12P 1/02; C12N 1/14
(52) U.S. Cl. .................. 424/405; 424/93.5; 424/115; 435/256.3; 435/254.1; 435/171; 504/117; 504/118
(58) Field of Search ................... 424/405, 93.5, 424/115; 435/256.3, 171, 254.1, 804; 504/117, 118

(56) References Cited

U.S. PATENT DOCUMENTS 5,041,384  8/1991  Wilson et al. .

FOREIGN PATENT DOCUMENTS

| 2110683 | 9/1972 | (DE) . |
| 226 471 | 8/1985 | (DE) . |
| 231 482 | 1/1986 | (DE) . |
| 3600394 | 7/1987 | (DE) . |
| 3801023 | 7/1989 | (DE) . |

OTHER PUBLICATIONS

Dutta, Plant Soil, vol. 63, No. 2, pp. 209–216, 1981.*
Jackson et al., Mycology Research, vol. 98, No. 10, pp. 1117–1126, 1994.*
Derwent Abstract 95–126070; 1995.
Derwent Abstract 97–81435; 1996.
Derwent Abstract 97–99456; 1997.
Derwent Abstract 94–89428; 1994.
Derwent Abstract 88–82239; 1987.
Derwent Abstract 94–163085; 1994.
Derwent Abstract 96–90232; 1996.
Derwent Abstract 87–206834/198730 (of) DE 3600349; 1987.
Derwent Abstract 86–113377/198618 (of) DD231482; 1986.
Derwent Abstract 72–59739T/197238 (of) DE 2110683; 1972.
Derwent Abstract 89–221281/198931 (of DE 3801023); 1989.

* cited by examiner

Primary Examiner—Francisco Prats
Assistant Examiner—Susan Coe
(74) Attorney, Agent, or Firm—William A. Teoli, Jr.

(57) ABSTRACT

The present invention provides an agent for inducing resistance against phytophathogenic microorganisms in plants wherein the agent is an extract of biomass from non-plant-pathogenic microorganisms obtainable by the following process: a) resuspending 50 g to 200 g (dry weight) of biomass from non-plant-pathogenic microorganisms per liter of inorganic or organic solvent; b) stirring at room temperature for 1 to 12 hours; c) incubating; d) resuspending; e) allowing to cool to room temperature; and f) optionally filtering.

13 Claims, No Drawings

PLANT IMMUNIZATION COMPOSITIONS

The present invention relates generally to plant immunization and, more particularly, to compositions and methods for inducing resistance against phytopathogenic microorganisms, such as phytopathogenic fungi, in plants.

BACKGROUND OF THE INVENTION

Various studies have indicated that the susceptibility of plants to certain diseases is not synonymous with the absence of the genetic potential for resistance mechanisms to those diseases. In fact, it is known that resistance can be induced in apparently susceptible plants by inoculation with avirulent forms of plant-pathogens, hypovirulent plant-pathogens or by restricted inoculation with plant-pathogens. The resulting induced resistance is persistent and generally non-specific for a pathogen.

This defense system is a complex interaction of early pathogenic recognition events generating signals which are transduced from the site of inoculation intra- and intercellularly throughout the entire plant. These signals trigger a series of inducible defense reactions with the aim of blocking or even killing the invading pathogen. Many defense reactions are controlled at the gene transcription level.

Pathogen detection takes place as close as possible to the plant surface. Cell-wall degradation products of the attacking pathogen (glucan elicitors) as well as fragments of the plant cell under attack (oligogalacturonide elicitors) are amongst the best described alarm signals. From the site of attack, secondary signals are spread all over the plant. The most documented compound within this signal chain is salicylic acid but electrical signals have also been described as defense inducing signals.

The defense reactions which are activated by incoming alarm signals cover a broad spectrum of chemical, biochemical, and mechanical defense. In monocotyledonous plants reinforcement of cell-walls by callose-deposits opposite to the point where a pathogen tries to penetrate is often observed. Induction of hydrolytic enzymes (e.g. chitinases with lysozyme activity, β-1,3-glucanases, proteases) is observed in di- and monocotyledonous plants. Plants can also react by synthesizing toxic secondary metabolites, so-called phytoalexins, in locally highly elevated concentration, which can kill invading microorganism. One of the earliest reactions of an attacked plant cell is the generation of active oxygen radicals, often a start of the complete sacrifice of a limited number of cells surrounding an infection site.

SUMMARY OF THE INVENTION

Surprisingly it has now been found that an extract of biomass from microorganisms which do not normally cause diseases on any plants (non-plant-pathogenic microorganisms) can be used for inducing resistance against phytopathogenic microorganisms in plants.

Accordingly, the invention provides an agent for inducing resistance against phytopathogenic microorganisms in plants wherein the agent is an extract of biomass from non-plant-pathogenic microorganisms obtainable by the following process:

a) suspending 50 g to 200 g (dry weight) of biomass from non-plant-pathogenic microorganisms per liter of inorganic or organic solvent;

b) stirring at room temperature for 1 to 12 hours;

c) incubating;

d) resuspending;

e) allowing to cool to room temperature; and f) optionally filtering.

(Hereinafter "agent of the invention")

Also provided are agricultural compositions comprising an agent obtainable by the above-described process in combination with agriculturally acceptable carrier materials (diluents) and optionally one or more plant pesticides capable of inducing resistance against phytophathological microorganisms in plants.

Also provided according to the present invention is an extract from *Penicillium chrysogenum* capable of inducing resistance against phytophathological microorganisms in plants.

The invention further provides a method of inducing resistance against phytopathogenic microorganisms in plants by applying the agent of the invention to plants, to soil or to seeds. The agent may be used as such, i.e. in un-formulated form, or in form of an agricultural composition.

The invention also provides a process for the production of an agent for inducing resistance against phytopathogenic microorganisms in plants wherein the agent is an extract of biomass from non-plant-pathogenic microorganisms which is obtained by:

a) resuspending 50 g to 200 g (dry weight) of biomass from non-plant-pathogenic microorganisms per liter of inorganic or organic solvent;

b) stirring at room temperature for 1 to 12 hours;

c) incubating;

d) resuspending;

e) allowing to coot to room temperature; and f) optionally filtering.

DETAILED DESCRIPTION OF THE INVENTION

By "plants" as used herein we mean typically cultivated plants, which are grown/raised to produce a harvestible product. Target plants to be protected by introducing resistance being within the scope of the present invention comprise, for example, the following species of plants: cereals (wheat, barley, rye, oats, rice, sorghum and related crops), beet (sugar beet and fodder beet), drupes, pomes and soft fruit (apples, pears, plums, peaches, almonds, cherries, strawberries, raspberries and blackberries), leguminous plants (beans, lentils, peas and soybeans), oil plants (rape, mustard, poppy, olives, sunflowers, coconuts, castor oil plants, cocoa beans and ground nuts), cucumber plants (cucumber, marrows and melons), fibre plants (cotton, flax, hemp and jute), citrus fruit (oranges, lemon, grapefruits and mandarins), vegetables (spinach, lettuce, asparagus, cabbage, carrots, onions, garlic, tomatoes, potatoes and pepper), lauraceae (avocados, cinnamon and camphor) or plants such as maize, tobacco, nuts, coffee, sugar cane, tea, vines, hops, bananas and natural rubber plants; also ornamentals, areas of grass (turf) and embankments.

Preferred plants to be protected according to the invention include: solanaceae such as tomato and potato, beans, cucumber, pepper, tobacco, groundnut and grape vines.

Particularly preferred plants to be protected according to the invention are the solanacea.

By "phytopathogenic microorganisms" as used herein we mean fungi, bacteria and viruses that attack plants and cause damage to the plant. The agent of the invention is particularly effective in inducing resistance to phytopathogenic fungi. Such phytopathogenic fungi include e.g. *Phytophthora infestans, Cladosporium fulvum, Plasmopora viticola, Colletotrichum lagenarium, Pseudomonas lachrymans* and *Puccinia tritici.*

With the agent of the invention particularly good results are achieveable in the protection of solanaceae such as tomato and potato against *Phytophthora infestans* and *Cladosporium fulvum* and in the protection of grape vines against *Plasmopora viticola* and in the protection of cucumber against *Colletotrichum lagenarium* and *Pseudomonas lachrymans.*

By "non-plant-pathogenic microorganisms" as used herein we mean microorganisms of these genera and species which do not cause disease in plants. Preferably the non-plant-pathogenic microorganisms are also non-plant-specific microorganisms, i.e. they do not grow on plants.

Examples of genera of microorganisms which can be used according to the invention include the following:

Bacteria: Acetobacter, Achromobacter, Actinoplanes, Aerobacter, Alcaligenes, Arthrobacter, Bacillus, Brevibacterium, Cephalosporium, Clostridium, Corynebacterium, Cryptococcus, Escherichia, Flavobacterium, Gluconobacter, Lactobacillus, Leuconostoc, Methanobacillus, Methanomonas, Methylovibrio, Microbacterium, Micrococcus, Micromonospora, Mycobacterium, Nocardia, Propionibacterium, Protaminobacter, Proteus, Pseudomonas, Rhodopseudomonas, Saccharopolyspora, Sarcina, Sporotrichum, Streptococcus, Streptomyces, Thermomonospora, Thiobacillus, Xanthomonas;

Fungi and Yeasts: Acremonium, Aschersonia, Ashbya, Aspergillus, Aureobasidium, Beaveria, Candida, Claviceps, Clitopilus, Curvularia, Cyclindrocarpon, Eremothecium, Enwinia, Fusarium, Fusidium, Gibberalia, Hansenula, Hirsutella, Klyveromyces, Metarhizium, Mucor, Myocandida, Neocosmospora, Phaecilomyces, Penicillium, Pericularia, Phanerochaete, Phycomyces, Pichia, Pullularia, Rhizopus, Saccharomyces, Schizosaccharomyces, Sclerotium, Sesquicilliopsis, Streptomyxa, Tolypocladium, Torula, Torulopsis, Trametes, Trichoderma, Trigonopsis.

Examples of particular species which can be used according to the invention include the following:

Bacteria: *Acetobacter aceti, Acetobacter suboxydans, Acetobacter xylinum, Achromobacter obae, Actinoplanes missouriensis, Aerobacter aerogenes, Alcaligenes faecalis, Arthrobacter hyalinus, Arthrobacter paraffineus, Arthrobacter simplex Bacillus acidocaldarius, Bacillus amyloliquefaciens, Bacillus amylosolvens, Bacillus brevis, Bacillus caldolyticus, Bacillus cereus, Bacillus circulans, Bacillus coagulans, Bacillus firmus, Bacillus lentus, Bacillus licheniformis, Bacillus megaterium, Bacillus megaterium, Bacillus moritae, Bacillus polymyxa, Bacillus popiliae, Bacillus pumilis, Bacillus subtilis, Brevibacterium amylolyticum, Brevibacterium flavum, Brevibacterium lactofermentum, Clostridium acetobutylicum, Clostridium butyricum, Corynebacterium gelatinosum, Corynebacterium glutamicum, Corynebacterium guanofaciens, Corynebacterium hydrocarboclastus, Corynebacterium petrophilum, Cryptococcus laurentii, Escherichia coli, Flavobacterium aminogenes, Gluconobacter melanogenus, Lactobacillus bulgaris, Lactobacillus delbrueckii, Lactobacillus helveticus, Lactobacillus leichmanii, Lactobacillus pentosus, Leuconostoc brevis, Leuconostoc dextranicum, Leuconostoc mesenteroides, Methanobacillus omelianski, Methanobacillus soenhngenii, Methanomonas margaritae, Methanomonas capsulatus, Methanomonas methanica, Methylovibrio soehngenii, Microbacterium ammoniaphilum, Micrococcus glutamicus, Micromonospora carbonaceae, Micromonospora echinospora, Micromonospora inyoensis, Micromonospora olivoasterospora, Micromonspura purpurea, Mycobactedium phlei, Mycobacterium smegmatis, Nocardia alkanoglutinosa, Nocardia gardneri, Nocardia mediterranei, Nocardia uniformis, Propionibacterium freudenreichii, Propionibacterium shermanii, Protaminobacter ruber, Proteus rettgeri, Pseudomonas amyloderamosa, Pseudomonas aureofaciens, Pseudomonas dacunhae, Pseudomonas denitrificans, Pseudomonas methylotrophus, Pseudomonas ovalis, Pseudomonas pyrrocinia, Rhodopseudomonas spheroides, Saccharopolyspora erythraea, Sarcina lutea, Sporotrichum pulverulentum, Streptococcus cremoris, Streptococcus fradiae, Streptococcus lactis, Streptococcus mutans, Streptococcus thermophilus,* Streptomyces all species, *Thermomonospora curvata, Thermomonospora fusca, Thiobacillus ferroxidans, Thiobacillus thiooxidans;*

Fungi and Yeasts: *Acremonium chrysogenum, Aschersonia aleyrodis, Ashbya gossypii, Aspergillus awamori, Aspergillus flavus, Aspergillus itaconicus, Aspergillus oryzae, Aspergillus sojae, Aspergillus terreus, Aspergillus wentii, Aureobasidium pullulans, Beauveria bassiana, Beauveria inflatum, Candida flareri, Candida lipolytica, Candida oleophila, Candida periculosa, Candida tropicalis, Candida utilis, Cephalosporium acremonium, Claviceps paspali, Claviceps fusiformis, Clitopilus passeckerianus, Curvularia lunata, Cyclindrocarpon radicicola, Eremothecium ashbyii, Hansenula anomala, Hirsutella thompsonii, Klyveromyces fragilis, Klyveromyces lactis, Metarhizium anisophae, Mucor miehei, Mucor pusillus, Myocandida riboflavina, Neocosmospora vasinfecta, Phaecilomyces vanioti, Penicillium chrysogenum, Penicillium camemberti, Penicillium griseofulvum, Penicillium roqueforti, Penicillium patulum, Phanerochaete chrysosporium, Phycomyces blakesleanus, Pichia guilliermondi, Pichia stiptis, Pullularia pullulans, Rhizopus delemar, Rhizopus formosaensi, Rhizopus japanicus, Rhizopus nigricans, Rhizopus niveus, Saccharomyces cerevisiae, Saccharomyces carlsbergiensis, Saccharomyces rouxii, Saccharomyces lipolytica, Schizosaccharomyces pombe, Sclerotium glutanicum, Sesquicilliopsis rosariensis, Streptomyxa affinis, Tolypocladium inflatum, Tolypocladium terricola, Torula cremoris, Torulopsis magnoliae, Torulopsis utilis, Trametes sanguinea, Trigonopsis variabilis.*

The non-plant-pathogenic microorganisms are preferably fungi or yeasts, but especially fungi.

Particularly preferred species of the fungi belong to the following genera and species: Acremonium spp like *Acremonium chrysogenum,* Aspergillus spp. like *Aspergillus awamori, Aspergillus itaconicus,* Aureobasidium spp. like *Aureobasidium pullulans,* Beauveria spp. like *Beauveria bassiana, Beauveria inflatum,* Clitopilus spp. like. *Clitopilus passeckerianus,* Mucor spp. like *Mucor miehei, Mucor pusillus,* Neocosmospera spp. like *Neocosmospera vasinfecta,* Phaecilomyces spp. like *Phaecilomyces varioti,* Penicillium spp. like *Penicillium chrysogenum, Penicillium camemberti, Penicillium citrinum, Penicillium griseofulvum, Penicillium roqueforti, Penicillium urticae, Penicillium patulum,* Phanerochaete spp. like *Phanerochaete chrysosporium,* Pullularia spp. like *Pullularia pullulans,* Schizosaccharomyces spp. like *Schizosaccharomyces pombe,* Tolypocladium spp. like *Tolypocladium inflatum, Tolypocladium terricola,* Trametes spp. like *Trametes sanguinea,* Trichoderma spp. like *Trichoderma koningii, Trichoderma reseei, Trichoderma viride.*

Even more preferred microorganisms which may be used according to the invention belong to the genera Penicillium and Cephalosporium of which the species *Penicillium chrysogenum* and *Cephalosporium acremonium* are particularly preferred.

By "biomass" as used herein we mean dried organic waste products that are obtained in a biotechnological fermentation process for e.g. the production of pharmaceuticals such as antibiotics. At the time of the harvest the wet microbiological biomass is separated by filtration from the liquid, e.g. antibiotic containing phase, and dried, e.g. during 4 to 6 hours at +130 to +150° C. This dried organic waste product can now serve as the starting material to produce the agent of the invention.

Preferably the starting material is fungal biomass (mycelia) which is derived from the waste products of biotechnological fermentation processes, preferably from the fermentation of *Penicillium chrysogenum* and *Cephalosporium acremonium*.

A preferred example of the inorganic solvent suitable for steps (a) and (d) of the extraction process is water. Preferred examples of the organic solvents suitable for use in steps (a) and (d) are alcohols such as isopropanol, ethanol or methanol.

Concentrations of 50 to 200 g (dry weight) of biomass from non-plant-pathogenic microorganisms per liter of solvent are generally used. Preferably about 150 g (dry weight) of biomass are suspended per liter of solvent.

The suspension resulting from step (a) will typically have a pH of about 2.8 to about 5.6, preferably of about 3.3 to about 3.6 without further adjustment. This suspension is in general stirred at room temperature (+20 to +25° C.) for 1 to 12 hours (step (b)).

Typical incubation conditions for step (c) are e.g. 1 hour at +120° C., 2 hours at +80° C., or 12 hours at +20° C. Whereby the maximum temperature is +120° C. and the minimum temperature is +20° C. At +120° C. the time period of incubation should not exceed 2 hours and not be less than 0.5 hours, whereas at +20° C. the minimum time period of incubation should be 8 hours and the maximum period 70 hours. The person skilled in the art will know how to determine minimum and maximum time periods of incubation at given temperatures between +120° C. and +20° C. Preferably incubation is carried out under simultaneous heating or autoclaving such as for 1 hour at +120° C. (the extract obtained from this route will hereafter be referred to as extract PEN-A) or for 2 hours at +80° C. The extract obtained from incubation for 12 hours at +20° C. will hereafter be referred to as extract PEN-B.

Resuspension in step (d) is typically carried out by shaking or mixing the suspension which may have been separated into solid and liquid components during step (c).

Step (e) is of course only necessary if the incubation temperature used is above room temperature.

Filtering in step (f) is typically carried out through paper filters resulting in a clear solution of a brownish color and an odor typical for fermentation products. The filtering step can also be carried out on industrial scale by batchwise or continuous centrifugation or by employing a filterpress. The filtering step serves i.a. to reduce the risk of phytotoxicity. Preferred agents of the invention are obtained by including the filtering step (f).

After step (e) or preferably the filtering step (f) the extract is conveniently dried so that it can be packaged and shipped in powder form and resuspended by the end user for use according to the invention. Drying conditions are not critical, any known methods such as lyophilisation, spray drying or rotation drying can be used.

Changes in the extraction procedure will lead to severe losses of the desired plant protectant activity and/or cause strong phytotoxic side effects of the extract.

The agent of the invention will typically comprise as active ingredients
1) branched or unbranched oligosaccharides of a degree of polymerization between two and 30 or larger,
2) monosaccharides, and
3) proteins, glycoproteins and/or lipoproteins.

Preferably the agent of the invention will contain:
1) 0.5 to 8.0 g/l of branched and unbranched oligosaccharides of a degree of polymerization between two and 30, mainly in beta 1–6 and beta 1–3 linkage,
2) 0.1 to 4.0 g/l of monosaccharides, and
3) 0.1 to 1,5 g/l of proteins, glycoproteins and/or lipoproteins.

The monomers released by hydrolysis of said oligosaccharides are mainly mannose, galactose and glucose in a ratio of e.g. 1:1:1 (for *Penicillium chrysogenum*), 2:1:2, 1:1:2 or 2:1:1, but also N-acetylglucosamine, glucosamine and chitin.

The major plant defense inducing activity is associated with molecules of a molecular weight of <3'000 dalton.

The invention also provides compositions for inducing resistance against phytopathogenic microorganisms in plants, comprising as active ingredient the agent of the invention in association with an agriculturally acceptable diluent (hereinafter diluent) and optionally one or more plant pesticides. The compositions are obtained in conventional manner, e.g. by mixing the agent of the invention with a diluent and optionally additional ingredients, such as surfactants.

The term diluents as used herein means liquid or solid agriculturally acceptable material, which may be added to the active agent to bring it in an easier or better applicable form, resp. to dilute the active agent to a usable or desirable strength of activity. Examples of such diluents are talc, kaolin, diatomaceous earth, xylene or water.

Especially formulations used in spray form such as water dispersible concentrates or wettable powders, may contain surfactants such as wetting and dispersing agents, e.g. the condensation product of formaldehyde with naphthalene sulphonate, an alkylarylsulphonate, a lignin sulphonate, a fatty alkyl sulphate, an ethoxylated alkylphenol and an ethoxylated fatty alcohol. In general, the formulations include from 0.01 to 90% by weight of active agent (agent of the invention and optional pesticides), from 0 to 20% agriculturally acceptable surfactant and from 10 to 99.99% diluent(s). Concentrated forms of composition, e.g. emulsion concentrates, contain in general from about 2 to 90%, preferably from between 5 and 70% by weight of active agent. Application forms of formulation contain in general from 0.0005 to 10% by weight of active agent of the invention as active agent typical spray-suspensions may, for example, contain from 0.0005 to 0.05, e.g. 0.001, 0.002 or 0.005% by weight of active agent.

In addition to the usual diluents and surfactants, the agent of the invention may comprise further additives with special purposes, e.g. stabilisers, desactivators (for solid formulations or carriers with an active surface), agents for improving the adhesion to plants, corrosion inhibitors, anti-foaming agents and colorants.

Suitable plant pesticides which can be used in combination with the agent of the invention include fungicides, herbicides, bactericides, insecticides, etc. The agent of the invention is preferably used in combination with fungicides, e.g. sulphur, chlorothalonil, euparen; a guanidine fungicide such as guazatine; dithiocarbamates such as mancozeb, maneb, zineb, propineb; trichloromethane sulphenylphthalimides and analogues such as captan, captafol and folpet; benzimidazoles such as carbendazim, benomyl; azoles such as difenoconazole, cyproconazole, flusilazole, flutriafol, hexaconazole, propiconazole, penconazole, tebuconazole, metaconazole, epoxiconazole, tetraconazole, triticonazole, probenazole, tricyclazole, fluquinconazole, prochloraz; morpholines such as fenpropimorph, fenpropidine, dimethomorph, or other beneficially-acting materials, such as fungicides like quinoxyfen, famoxyadone, spiroxamine, fenhexamide, 2-(2-phenoxyphenyl)-(E)-2-methoximino-N-methylacetamide, [2-(2,5-dimethylphenoxymethyl)-phenyl]-(E)-2-methoximino-N-methylamide, (1R,3S/1S, 3R)-2,2-dichloro-N-[(R)-1-(4-chlorphenyl)-ethyl]-1-ethyl-3-methylcyclopropancarboxamide, methoxyacrylates and methoximinoacrylates as disclosed in formula I of WO97/00011, azoxystrobin, kresoxiom-methyl, cymoxanil, cyprodinil, pyroquilon, oxadixyl, metalaxyl, or R-metalaxyl, or such as insecticides like furathiocarb or compounds as disclosed in formula I of EP-A-0580553, whereby the combinations with cyproconazole, propiconazole, R-metalaxyl, or oxadixyl are preferred.

Such combinations are particularly effective in treating and preventing outbreaks of late blight (*Phytophthora infestans*), anthrocnose (*Colletotnchum lagenarium*), rust (*Puccinia tritici*), mildew (*Erysiphe graminis*), bacterial wilt (*Erwinia tracheiphila*), and angular leaf spot (*Pseudomonas lachrymans*).

Examples of plant fungicide formulations are as follows:
a. Wettable Powder Formulation 10 Parts of the agent of the invention in dried form are mixed and milled with 4 parts of synthetic fine silica, 3 parts of sodium lauryl sulphate, 7 parts of sodium lignin sulphonate and 66 parts of finely divided kaolin and 10 parts of diatomaceous earth until the mean particle size is about 5 micron. The resulting wettable powder is diluted with water before use to a spray liquor which may be applied by foliar spray as well as by root drench application.
b. Granules Onto 94.5 parts by weight of quartz sand in a tumbler mixer are sprayed 0.5 parts by weight of a binder (non-ionic tenside) and the whole thoroughly mixed. 5 parts by weight of a agent of the invention in dried form are then added and thorough mixing continued to obtain a granulate formulation with a particle size in the range of from 0.3 to 0.7 mm (where required, the granules may be dried by the addition of 1 to 5% by weight of talcum). The granules may be applied by incorporation into the soil adjacent to the plants to be treated.
c. Emulsion Concentrate 10 Parts by weight of the agent of the invention are mixed with 10 parts of weight of an emulsifier and 80 parts by weight of xylene. The thus obtained concentrate is diluted with water to form an emulsion of the desired concentration, prior to application.
d. Seed Dressing 45 Parts of the agent of the invention are mixed with 1.5 parts of diamyl phenoldecaglycolether ethylene oxide adduct, 2 parts of spindle oil, 51 parts of fine talcum and 0.5 parts of colorant rhodamin B. The mixture is ground in a contraplex mill at 10,000 rpm until an average particle size of less than 20 microns is obtained. The resulting dry powder has good adherence and may be applied to seeds, e.g. by mixing for 2 to 5 minutes in a slowly turning vessel.

The agent of the invention may be applied to plants by spraying on leaf and/or stem surfaces, it may be applied to the soil by drenching the soil or by working granules or encapsulations into the soil and it may be applied to seeds by applying it as seed dressing.

The preferred mode of application is by spraying on leaf and/or stem surfaces or by a combination of alternating spraying on leaf and/or stem surfaces and drenching the soil.

When the agent of the present invention is applied by spraying on leaft and stem surfaces it may also contain further ingredients such as adjuvants, stabilizers, surfactants and tackifiers known in the art.

When the composition is applied as seed dressing this may be done in combination with adhesives or the active agent may be used in encapsulated form, which may be achieved by known encapsulation techniques.

The amount of the agent of the invention to be applied is typically 0.005 to 1.0 g of glucose equivalents per plant, or alternatively 0.05 to 2 kg per ha and treatment. Repeated treatment might be necessary. Glucose equivalents are determined by determined by the "Anthron" procedure with glucose as standard [Dische, Z (1962) Color Reactions of Carbohydrates. In Methods in Carbohydrate Chemistry. Vol. (Whistler, R. L. Wolfrom, M. L., eds.) Academic Press Inc. New York].

The concentration at which the extract is applied to induce resistance in plants is typically from 0.5 to 3.0 g/l of glucose equivalents.

The degree of protection is calculated with respect to control plants according to the following formula:

$$\% \text{ protection} = \frac{\% \text{ infested leaf surface}_{control} - \% \text{ infested leaf surface}_{treated}}{\% \text{ infested leaf surface}_{control}} \times 100$$

The following examples are presented to demonstrate the invention. The examples are intended to be illustrative and not limitative.

EXAMPLE 1

Preparation of an Extract from Penicillium 300 g dry weight of *Penicillium chrysogenum* mycelium waste, from penicillin production are transferred into a 2000 ml Duran® glass bottle to which distilled water is added to a final volume of 2 liter (pH of the solution is 3.2). The resulting suspension is stirred at room temperature for 1 h at 700 rpm and then autoclaved for 1 h at +121° C. and 1 bar. Thereafter the still hot bottle is shaked carefully and let cool and settle over night. Then the whole content of the bottle is filtered through Melitta® paper coffee filter 1×10 and the liquid flow-through which contains the active extract (hereafter referred to as PEN-extract) is collected. The sugar content (glucose equivalents) of the extract is determined by the "Anthron" procedure with glucose as standard [Dische, Z (1962) Color Reactions of Carbohydrates. In Methods in Carbohydrate Chemistry. Vol. (Whistler, R. L. Wolfrom, M. L., eds.) Academic Press Inc. New York]. A typical PEN-extract contains about 5 g glucose equivalents per liter and is typically 2–3 times diluted before being applied to the test plant.

EXAMPLE 2

Treatment of Tomato against *Phytophthora infestans*
Plant and fungal material;

Tomato (*Lycopersicum esculentum*) plant of the variety "Baby F1" are grown in a greenhouse in a 120 cavity seed bed in a mixture of ⅓ sand and ⅔ TKS1® soil at +25° C. in a 16 h daylight/8 h dark regime. After 14 days individual seedlings are transferred to pots of 10 cm diameter and kept under the same growing conditions for another three weeks.

A *Phytophthora infestans* strain is cultivated on bi-concavely cut potato tuber slices (cultivar Bintije from biological farming) in closed plastic trays in the dark at +12 to +16° C. and 60–80% relative humidity for 6 to 7 days.

Inoculum suspension is prepared by washing potato tuber slices which were totally covered with sporulating Phytophthora infestans mycelium in 100 ml of ice-cold distilled water. Mycelium debris is removed by filtration and the amount of sporangia in the wash-through determined by counting in a "Neubauer" counting chamber under a microscope.

The inoculum density is adjusted to 30–40,000 sporangia per ml immediately before inoculation.

Treatment;

Tomato plants at the five true leaf stage are either drenched and/or sprayed with PEN extract 7 and 3 days before inoculation with *Phytophthora infestans* sporangia suspension.

Drench: Plants are kept dry for one day ahead of the treatment and the pots placed in 7×7 cm trays in order to collect excess drench solution. 60 ml of PEN extract containing 1 to 2 g of glucose equivalents per liter are applied at room temperature in the greenhouse.

Spray: The entire plant is sprayed with PEN-extract containing 1–2 g of glucose equivalents to near run-off (about 10–15 ml per plant) with an air driven spray pistol, model JATO 232 FR at 0.5 bar.

After the treatment plants are kept in the greenhouse till they are challenge inoculated. Control plants were mock treated with distilled water.

Challenge Inoculation;

Treated or control plants are sprayed with approximately 10 ml of ice-cold sporangia suspension in a ventilated inoculation chamber using an air driven spray pistol, model JATO 232 FR at 0.2 bar covering mainly the lower leaf surfaces with a homogeneous layer of fine troplets.

Immediately after inoculation plants are transferred to Plexiglas boxes and kept at +12 to +16° C. and a 100% relative humidity for 24 h in the dark. Afterwards they are returned to the greenhouse and kept at standard conditions as described above.

Evaluation;

5 to 6 days after inoculation, when typical symptoms became visible on control plants the degree of infection was visually determined as % of infected leaf area on the lower five leaves of the test plants. The degree of protection was calculated with respect to the control plants according to the formula:

$$\%\ protection = \frac{\%\ infested\ leaf\ surface_{control} - \%\ infested\ leaf\ surface_{treated}}{\%\ infested\ leaf\ surface_{control}} \times 100$$

Results are shown in Table Ia. Best Results are achieved with a combined drench and spray application.

TABLE Ia

Induced Plant Defense on tomato against *Phytophthora infestans* with PEN in drench and spray application and in combined drench/spray applications

| Treatment° | Concentration of PEN | % infected leaf area | % protection |
|---|---|---|---|
| D + S | 1.5 g/l, 2.0 g/l | 4 | 91 |
| D + S | 1.5 g/l, 1.0 g/l | 10 | 75 |
| D + S | 1.5 g/l, 0.5 g/l | 23.3 | 50.1 |
| D + S* | 2.0 g/l, 1.5 g/l | 8 | 89 |
| 2 D | 1.5 g/l | 40 | 14.3 |
| 1 D | 1.5 g/l | 18.3 | 60.8 |
| 2 S | 1.5 g/l | 10 | 78.6 |
| 1 S | 1.5 g/l | 16.7 | 64.2 |
| control, water | | 47 | |
| *control, water | | 73 | |

Values are means of four independent experiments. The error of the mean is ≦9.5%. D = drench, S = spray. °First treatment 7 days prior inoculation, second treatment 3 days prior inoculation. *This value comes from a different experiment and therefore also has a different control value as seen in the last line of Table Ia.

EXAMPLE 3

Treatment of Potato against *Phytophtora infestans*

Using the same procedure as in Example 2 plant defence against *Phytophthora infestans* was induced in potato plants grown from tubers of the variety "Bintje" at the four leaf stage. Results are shown in Table Ib. Best results were achieved with spray application.

TABLE Ib

Induced Plant Defense on potato against *Phytophthora infestans* with PEN in spray application and in combined drench/spray applications

| Treatment* | Concentration of PEN | % infected leaf area | % protection |
|---|---|---|---|
| 1 D + 1 S | 2 g/l, 2 g/l | 10 | 83 |
| 1 D + 1 S | 1 g/l, 1 g/l | 20 | 67 |
| 2 S | 3 g/l | 7 | 89 |
| 2 S | 2 g/l | 3 | 95 |
| 2 S | 1 g/l | 8 | 86 |
| 2 S | 0.5 g/l | 27 | 56 |
| BABA | 500 ppm | 23 | 61 |
| control, water | | 61 | 0 |

Values are means of three independent experiments. The error of the mean is ≦11%. D = drench, S = spray. *First treatment 7 days prior inoculation, second treatment 3 days prior inoculation. BABA = beta-butyric acid was used as a standard chemical inducer.

EXAMPLE 4

Treatment of Bean Plants against *Uromyces appendiculatus*

Plant and Fungal Material;

Two bean (*Phaseolus aureus*) seeds of the variety "Musica" were grown in a pots of 8 cm diameter in a mixture of ⅓ sand and ⅔ TKS1 soil at +25° C. in a 16/8 h light/dark regime. for 16 days. One seedling per pot was selected for the assay just before unfolding of the secondary leaves.

Spores of a *Uromyces appendiculatus* strain were taken from the KRYO liquid nitrogen storage. 1 mg of spores yielded 1 ml of inoculation suspension.

Treatment;

Bean plants at the secondary leaf stage were either drenched and/or sprayed 7 and 3 days before inoculation with *Uromyces appendiculatus* sporangia suspension.

Drench: Plants were kept dry for one day ahead of the treatment and the pots placed in 7×7 cm trays in order to collect excess drench solution. 40 ml of PEN extract containing 1 to 2 g of glucose equivalents per liter. Following the treatment plants were kept in the greenhouse at +20 to +25° C. without watering for one day.

Spray: The entire plant was sprayed with PEN extract containing 1–2 g of glucose equivalents to near run-off with an air driven spray pistol, model JATO 232 FR at 0.5 bar.

After the treatment plants were kept in the greenhouse till they were challenge inoculated. Control plants were mock treated with distilled water.

Challenge Inoculation;

Treated or control plants were sprayed with approximately 3 ml of sporangia suspension in a ventilated inoculation chamber using an air driven spray pistol, model JATO 232 FR at 0.2 bar covering the lower leaf surfaces with a homogeneous layer of fine troplets.

Immediately after inoculation plants were transferred to Plexiglas boxes and kept at +20° C. and a 60% relative humidity for 24 h in the dark then light was switched on and the plants kept under the same conditions for additional four days. Afterwards plants were returned to the greenhouse and kept at standard conditions as described above. Non-inoculated leaves were removed.

Evaluation;

Two weeks after inoculation, when the fungus sporulated on control plants, the degree of infection was visually determined as % of infected leaf area on the inoculated leaves. The degree of protection was calculated with respect to the control plants according to the formula:

$$\% \text{ protection} = \frac{\% \text{ infested leaf surface}_{control} - \% \text{ infested leaf surface}_{treated}}{\% \text{ infested leaf surface}_{control}} \times 100$$

Results are given in Table II. Best results are achieved with 2 drench applications at 2 g/l or 0.5 g/l.

TABLE II

Induced Plant Defense on beans against *Uromyces appendiculatus* by spray treatment with PEN in drench and spray application and in combined drench/spray applications

| Treatment* | Concentration of PEN | % infected leaf area | % protection |
| --- | --- | --- | --- |
| 2D | 2 g/l | 5 | 95 |
| 2D | 1 g/l | 60 | 37 |
| 2D | 0.5 g/l | 3 | 97 |
| 1D + 1S | 2 g/l | 17 | 82 |
| 1D + 1S | 1 g/l | 33 | 65 |
| 1D + 1S | 0.5 g/l | 50 | 47 |
| 2S | 2 g/l | 27 | 72 |
| 2S | 1 g/l | 90 | 5.3 |
| 2S | 0.5 g/l | 60 | 37 |
| control, water | | 87 | 9 |

Values are means of two independent experiments using 4 individual plants each. The error of the mean is ≦ 8.5%.
D = drench,
S = spray.
*First treatment 7 days prior inoculation, second treatment 3 days prior inoculation.

EXAMPLE 5

Treatment of Wheat Against *Puccinia recondita* spp. tritici

Plant and Fungal Material;

Ten seeds of wheat (*Triticum arvense*) of the variety "Arina" were grown in pots of 8 cm diameter in a mixture of ⅓ sand and ⅔ TKS1® soil at +25° C. in a 16/8 h light/dark regime. for 7 days till the primary leaf was fully expended.

Brown rust strain *Puccinia recondita* spp. tritici was propagated on the same variety of wheat. Fully infected, sporulating leaves were cut and the spores dusted onto water containing 0.05% of Tween 20®. The inoculum density was adjusted to 100,000 spores per ml.

Treatment;

Wheat plants with the secondary leaf just emerging were sprayed 7 and 3 days before inoculation. The entire plant was sprayed with PEN extract containing 1–2 g of glucose equivalents and 0.05% of Tween 20 to near run-off with an air driven spray pistol, model JATO 232 FR at 0.5 bar.

After the treatment plants were kept in the greenhouse till they were challenge inoculated. Control plants were mock treated with distilled water.

Challenge Inoculation;

Treated or control plants were sprayed with approximately 3 ml of sporangia suspension in a ventilated inoculation chamber using an air driven spray pistol, model JATO 232 FR at 0.2 bar to generate a homogeneous layer of fine troplets on the whole seedling.

When the troplets had dried, plants were transferred to Plexiglas boxes and kept at +20° C. and a 60% relative humidity for 24 h in the dark then light was switched on and the plants kept under the same conditions for additional four days. Afterwards plants were returned to the greenhouse and kept at standard conditions as described above.

Evaluation;

10 days after inoculation, when the fungus sporulated on control plants, the degree of infection was visually determined as % of infected leaf area on the inoculated leaves plants. The degree of protection was calculated with respect to the control plants according to the formula:

$$\% \text{ protection} = \frac{\% \text{ infested leaf surface}_{control} - \% \text{ infested leaf surface}_{treated}}{\% \text{ infested leaf surface}_{control}} \times 100$$

Results are given in Table III. Best results are achieved by applying a fraction of PEN having a molecular weight of 2–3 kD at a concentration of 2 g/l.

TABLE III

Induced Plant Defense on wheat against *Puccinia recondita* spp. *Tritici* by spray treatment with PEN and molecular size fractions of PEN

| Treatment | Concentration | % infected | % protection |
| --- | --- | --- | --- |
| PEN | 2 g/l | 15.9 | 73.9 |
| PEN | 1 g/l | 42.2 | 30.9 |
| PEN > 30 kD | 4 g/l | 21.4 | 65 |
| PEN > 10 kD | 2 g/l | 33.3 | 45.5 |
| PEN > 10 kD | 1 g/l | 25 | 59 |
| PEN 2–3 kD | 2 g/l | 8.9 | 85.4 |
| PEN 2–3 kD | 1 g/l | 20 | 67.3 |
| PEN > 300 D | 1 g/l | 11.1 | 81.3 |
| PEN > 300 D | 0.5 g/l | 33.3 | 45.5 |
| CGA 245 704 | 30 ppm | 31.3 | 48.8 |
| CGA 245 704 | 60 ppm | 60 | 20 |
| formulation control | | 42.9 | 29.8 |
| water control | | 61.1 | 0 |

Values are means of four independent experiments. The error of the mean is ≦10%. CGA 245 704 the active ingredient of BION ® was used as a chemical standard inducer.

EXAMPLE 6

Treatment of Cucumber Against *Colletotrichum lagenarium* and *Pseudomonal lachrymans*

Plant/pathogen material.

Cucumber (*Cucumis sativus*) cv Wisconsin plants are grown in the greenhouse for 10 days in 40 ml pots. *Colletotrichum lagenarium* is grown on V8-vegetable-juice agar for 7 days at +20° C. on Petri-dishes. *Pseudomonas lachrymans* is grown on YDC—Medium (yeast-dextrose-calciumcarbonate) for 24 h at +30° C. in Erlenmeyer flasks.
Treatment A spray solution containing 1.5 or 3 g/l glucose-equivalents of PEN-A or PEN-B extract are sprayed onto the foliage using a special spray hood to near run-off. After the treatment, plants are incubated in the greenhouse at +22° C. for 3 or 7 days. Control plants are treated with water.
Challenge Inoculation A spore suspension of *C. lagenarium* (1.2. $10^5$ spores/ml) is sprayed onto the plant foliage using a Velbiss spray gun. Plants are incubated for 30 hours under 95% relative humidity (RL) in the dark at +23° C. Then plants are transferred to a greenhouse with +22 to +23° C. at normal RL.

A suspension of *P. lachrymans* ($10^8$ cells/ml) is sprayed onto the foliage using a Velbiss spray gun at a pressure of 2 bar. Before inoculation plants were incubated at 100% RL for 4 hours. After the inoculation, plants are again incubated in the greenhouse at 100% RL at 23 to +24° C.
Evaluation After 6 (*P. lachrymans*) or 7–8 (*C. lagenarium*) days, the disease is rated visually and % attacked leaf surface are estimated. The results are compiled in the following table.

| % preventive activity | PEN-A | | PEN-B | |
|---|---|---|---|---|
| treatment days before inoculation | 1.5 g/l | 3.0 g/l | 1.5 g/l | 3.0 g/l |
| Colletotrichum/cucumber 3 days | 96 | 92 | 98 | 96 |
| Colletotrichum/cucumber 7 days | 0 | 95 | 0 | 0 |
| Pseudomonas/cucumber 3 days | 10 | 10 | 80 | 35 |
| Pseudomonas/cucumber 7 days | 0 | 20 | 20 | 20 |

What is claimed is:

1. An agent for inducing resistance against phytopathogenic microorganisms in plants wherein the agent is an extract of a biomass, said biomass being derived from a biotechnological fermentation process, from non-plant-pathogenic microorganisms, not including microorganisms of the Saccharomyces genus, wherein said fermentation process results in a wet biomass phase and a liquid phase, said wet biomass is separated from said liquid phase by filtration and dried for at least 4 hours at a temperature of at least 130° C. to give a dried biomass, said agent obtainable from said dried biomass by the following process:
    a) resuspending 50 g to 200 g (dry weight) of said dried biomass per liter of inorganic or organic solvent to yield a suspension;
    b) stirring said suspension at room temperature for 1 to 12 hours;
    c) incubating said suspension;
    d) resuspending the result of step c;
    e) allowing the result of step d to cool to room temperature; and
    f) optionally filtering the result of step e.

2. An agent according to claim 1 wherein the biomass from non-plant pathogenic microorganisms is fungal biomass which is derived from the waste products of biotechnological fermentation processes.

3. An agent according to claim 1 wherein the non-plant pathogenic microorganism is a non-plant specific microorganism.

4. An agent according to claim 1 wherein the biomass is derived from the fermentation of Acremonium spp., Aspergillus spp., Aureobasidium spp., Beauveria spp., Clitopilus spp., Murcor spp., Neocosmospera spp., Phaecilomyces spp., Penicillium spp., Phanerochaete spp., Pullularia spp., Schizosaccharomyces spp., Tolypocladium spp., Trametes spp., and Trichoderma spp.

5. An agent according to claim 1 wherein the biomass is derived from the fermentation of *Penicillium chrysogenum* and *Cephalosporium acremonium*.

6. An agent according to claim 1 wherein the biomass is derived from the fermentation of *Penicillium chrysogenum*.

7. An agent according to claim 1, comprising as active ingredients
    1) branched or unbranched oligosaccharides of a degree of polymerization between two and 30,
    2) monsaccharides, and
    3) proteins, glycoproteins and/or lipoproteins having a molecular weight of <3,000 dalton.

8. A composition for inducing resistance against phyopathological microorganisms in plants which comprises a effective amount of a plant resistance inducing agent according to claim 1 and an agriculturally acceptable diluent.

9. A composition according to claim 8 which further comprises one or more plant pesticides.

10. A method of inducing resistance against phytopathological microorganisms in plants by applying an effective amount of the agent as defined in claim 1 to plants, to the soil or to seeds.

11. An extract from *Penicillium chrysogenum* capable of inducing resistance against phytopathological microorganisms in plants.

12. An extract from *Penicillium chrysogenum* capable of inducing resistance against phytopathological microorganisms in plants, wherein the extract is of a biomass, said biomass being derived from a biotechnological fermentation process, from non-plant-pathogenic microorganisms, not including microorganisms of the Saccharomyces genus, wherein said fermentation process results in a wet biomass phase and a liquid phase, said wet biomass is separated from said liquid phase by filtration and dried for at least 4 hours at a temperature of at least 130° C. to give a dried biomass, said extract obtainable from said dried biomass by the following process:
    (a) resuspending 50 g to 200 g (dry weight) of said dried biomass from *Penicillium chrosogenium* per liter of inorganic or organic solvent to yield a suspension;
    (b) stirring said suspension at room temperature for 1 to 12 hours;
    (c) incubating said suspension;
    (d) resuspending the result of step c;
    (e) allowing the result of step d to cool to room temperature; and
    (f) optionally filtering the result of step e.

13. An extract according to claim 12 wherein the concentration is from 0.5 to 3.0 g/l glucose equivalents.

* * * * *